United States Patent [19]

Matzke et al.

[11] Patent Number: 5,935,988

[45] Date of Patent: Aug. 10, 1999

[54] TOLERABILITY OF PHARMACEUTICALLY ACTIVE β-AMINO ACIDS

[75] Inventors: Michael Matzke, Wuppertal; Hans-Christian Militzer, Bergisch Gladbach; Joachim Mittendorf, Wuppertal; Franz Kunisch, Odenthal; Axel Schmidt, Wuppertal; Wolfgang Schönfeld, Wuppertal; Karl Ziegelbauer, Wuppertal, all of Germany

[73] Assignee: Bayer Aktiengesellschaft, Leverkusen, Germany

[21] Appl. No.: 08/679,027

[22] Filed: Jul. 12, 1996

[30] Foreign Application Priority Data

Jul. 19, 1995 [DE] Germany ............................ 195 26 274

[51] Int. Cl.⁶ .................................................. A61K 31/40
[52] U.S. Cl. .......................... 514/423; 514/561; 548/535; 558/432; 560/38; 560/48; 560/122; 560/125; 560/153; 560/168; 560/170; 560/171; 562/443; 562/457; 562/504; 562/507; 564/164; 564/189
[58] Field of Search ....................... 562/504, 457, 562/507, 443; 560/48, 122, 125, 38, 153, 168, 170, 171; 564/164, 189; 558/432; 548/535; 514/423, 561

[56] References Cited

U.S. PATENT DOCUMENTS 5,037,809  8/1991  Miyauchi .............................. 514/561
5,631,291  5/1997  Mittendorf ............................ 514/561

FOREIGN PATENT DOCUMENTS

| 0571870 | 12/1993 | European Pat. Off. . |
|---|---|---|
| 4302155 | 7/1994 | Germany . |
| 195 48 48 825 A1 | 7/1997 | Germany . |
| 196 04 225 A1 | 8/1997 | Germany . |
| WO 95/07022 | 3/1995 | WIPO . |

OTHER PUBLICATIONS

Derwent Abstract of JP 2–174–753, Agricultural Chemistry, p. 4, Derwent Week 9033 (1990).

H. Ohki, et al. J. Antibiot. vol. 44, No. 5, pp. 546–549 (1991).

*Primary Examiner*—Michael L. Shippen
*Attorney, Agent, or Firm*—Sprung Kramer Schaefer & Briscoe

[57] ABSTRACT

The present invention relates to mixtures of α-amino acids and/or derivatives thereof and cyclopentane-β-amino acids and/or derivatives thereof, dipeptides of the abovementioned α-amino acids and cyclopentane-β-amino acids and mixtures of the abovementioned mixtures and dipeptides which have an improved tolerability in warm-blooded animals compared with the pure cyclopentane-β-amino acids.

3 Claims, No Drawings

TOLERABILITY OF PHARMACEUTICALLY ACTIVE β-AMINO ACIDS

Cyclopentane- and -pentene-β-amino acids are known from the publications EP-A-571 870, DOS 43 02 155, JP 021 747 53 A2 and J. Antibiot. (1991), 44 (5), 546-9. Such β-amino acid compounds have an antimicrobial, in particular antimycotic, action. However, they are not free from side effects.

Surprisingly, it has now been found th mixtures of α-amino acids and/or derivatives thereof and cyclopentane-β-amino acids and/or derivatives thereof, dipeptides from the abovementioned α-amino acids and the abovementioned cyclopentane-β-amino acids and mixtures of the abovementioned mixtures and the abovementioned dipeptides do not have these undesirable side effects or have them to only a lesser extent and an improved tolerability in warm-blooded animals is thus achieved.

The present invention therefore relates to mixtures comprising one or more α-amino acids and/or derivatives thereof and one or more cyclopentane-β-amino acids and/or derivatives thereof The term "derivative" includes those compounds which are derived from the corresponding amino acids and have a comparable action, in particular the corresponding salts.

Suitable α-amino acids for the mixtures according to the invention are preferably α-amino acids of the general formula (Ia)

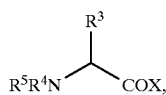

(Ia)

in which
  $R^3$ represents cycloalkyl having 3 to 8 carbon atoms, or represents aryl having 6 to 10 carbon atoms or hydrogen, or represents straight-chain or branched alkyl having up to 8 carbon atoms,
    where the alkyl is optionally substituted by cyano, methylthio, hydroxyl, mercapto, guanidyl or by a group of the formula —$NR^7R^8$ or $R^9$—OC—,
  wherein
    $R^7$ and $R^8$ independently of one another denote hydrogen, straight-chain or branched alkyl having up to 8 carbon atoms or phenyl,
  and
    $R^9$ denotes hydroxyl, benzyloxy, alkoxy having up to 6 carbon atoms or the abovementioned group —$NR^7R^8$, or the alkyl is optionally substituted by cycloalkyl having 3 to 8 carbon atoms or by aryl having 6 to 10 carbon atoms, which in its turn is substituted by hydroxyl, halogen, nitro, alkoxy having up to 8 carbon atoms or by the group —$NR^7R^8$,
  wherein
    $R^7$ and $R^8$ have the abovementioned meanings,
  $R^4$ and $R^5$ represent hydrogen
or
  $R^3$ and $R^4$ together form a radical of the formula —$(CH_2)_3$—,
  $R^5$ represents hydrogen and
  X represents hydroxyl, aryloxy having 6 to 10 carbon atoms, alkoxy having up to 6 carbon atoms or the group —$NR^7R^8$,
wherein
  $R^7$ and $R^8$ have the abovementioned meanings.

α-Amino acids which are particularly preferably suitable are those of the general formula (Ia)

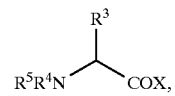

(Ia)

in which
  $R^3$ represents straight-chain or branched alkyl having up to 6 carbon atoms, which is optionally substituted by hydroxyl or phenyl, which in its turn can be substituted by hydroxyl,
  $R^4$ and $R^5$ represent hydrogen
or
  $R^3$ and $R^4$ together form a radical of the formula —$(CH_2)_3$—,
  $R^5$ represents hydrogen
and
  X represents hydroxyl.

α-Amino acids which are especially preferably suitable are those of the general formula (Ia)

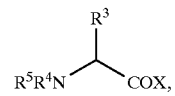

(Ia)

in which
  $R^3$ represents methyl, or represents a group of the formula —$CH(CH_3)CH_2CH_3$,
  $R^4$ and $R^5$ represent hydrogen
or
  $R^3$ and $R^4$ together form a radical of the formula —$(CH_2)_3$—,
  $R^5$ represents hydrogen and
  X represents hydroxyl.

Examples of such α-amino acids which may be mentioned are: (S)-isoleucine, (S)-alanine and (S)-proline.

Suitable cyclopentane-β-amino acids for the mixtures according to the invention are preferably cyclopentane-β-amino acids of the general formula (Ib)

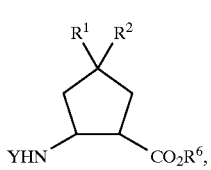

(Ib)

in which
  $R^1$ and $R^2$ represent hydrogen or
  $R^1$ and $R^2$ together form a radical of the formula =$CH_2$,
  $R^6$ represents hydrogen, or represents straight-chain or branched alkyl having up to 8 carbon atoms or phenyl and
  Y represents hydrogen, straight-chain or branched alkyl having up to 8 carbon atoms or aryl.

Cyclopentane-β-amino acids which are particularly preferably suitable are those of the general formula (Ib)

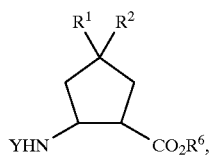

(Ib)

in which
R¹ and R² represent hydrogen or
R¹ and R² together form a radical of the formula =CH₂,
R⁶ represents hydrogen, or represents straight-chain or branched alkyl having up to 6 carbon atoms or phenyl and
Y represents hydrogen.

Cyclopentane-β-amino acids which are especially preferably suitable are those of the general formula (Ib)

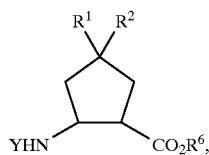

(Ib)

in which
R¹ and R² represent hydrogen or
R¹ and R² together form a radical of the formula =CH₂,
R⁶ represents hydrogen and
Y represents hydrogen.

Examples which may be mentioned of such cyclopentane-β-amino acids are: 2-amino-4-methylenecyclopentane-1-carboxylic acid and 1,2-cis-aminocyclopentane-1-carboxylic acid.

Preferred mixtures according to the invention comprise α-amino acids of the general formula (Ia)

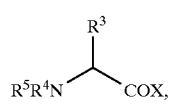

(Ia)

in which
R³ represents cycloalkyl having 3 to 8 carbon atoms, or represents aryl having 6 to 10 carbon atoms or hydrogen, or represents straight-chain or branched alkyl having up to 8 carbon atoms,
where the alkyl is optionally substituted by cyano, methylthio, hydroxyl, mercapto, guanidyl or by a group of the formula —NR⁷R⁸ or R⁹—OC—,
wherein
R⁷ and R⁸ independently of one another denote hydrogen, straight-chain or branched all having up to 8 carbon atoms or phenyl,
and
R⁹ denotes hydroxyl, benzyloxy, alkoxy having up to 6 carbon atoms or the abovementioned group —NR⁷R⁸,
or the alkyl is optionally substituted by cycloalkyl having 3 to 8 carbon atoms or by aryl having 6 to 10 carbon atoms, which in its turn is substituted by hydroxyl, halogen, nitro, alkoxy having up to 8 carbon atoms or by the group —NR⁷R⁸, wherein
R⁷ and R⁸ have the abovementioned meanings,
R⁴ and R⁵ represent hydrogen
or
R³ and R⁴ together form a radical of the formula —(CH₂)₃—,
R⁵ represents hydrogen and
X represents hydroxyl, aryloxy having 6 to 10 carbon atoms, alkoxy having up to 6 carbon atoms or the group —NR⁷R⁸,
wherein
R⁷ and R¹ have the abovementioned meanings,
and
cyclopentane-β-amino acids of the general formula (Ib)

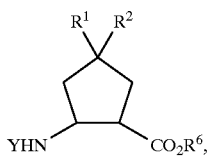

(Ib)

in which
R¹ and R² represent hydrogen or
R¹ and R² together form a radical of the formula =CH₂,
R⁶ represents hydrogen, or represents straight-chain or branched alkyl having up to 8 carbon atoms or phenyl and
Y represents hydrogen, straight-chain or branched alkyl having up to 8 carbon atoms or aryl.

Particularly preferred mixtures according to the invention comprise α-amino acids of the general formula (Ia)

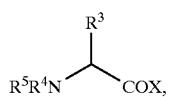

(Ia)

in which
R³ represents straight-chain or branched alkyl having up to 6 carbon atoms, which is optionally substituted by hydroxyl or phenyl, which in its turn can be substituted by hydroxyl,
R⁴ and R⁵ represent hydrogen
or
R³ and R⁴ together form a radical of the formula —(CH₂)₃—,
R⁵ represents hydrogen
and
X represents hydroxyl,
and cyclopentane-β-amino acids of the general formula (Ib)

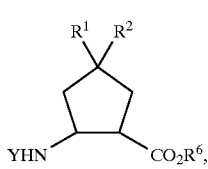

(Ib)

in which $R^1$ and $R^2$ represent hydrogen or $R^1$ and $R^2$ together form a radical of the formula =CH$_2$, $R^6$ represents hydrogen, or represents straight-chain or branched alkyl having up to 6 carbon atoms or phenyl and Y represents hydrogen.

Especially preferred mixtures comprise α-amino acids of the general formula (Ia)

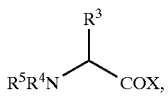
(Ia)

in which $R^3$ represents methyl, or represents a group of the formula —CH(CH$_3$)CH$_2$CH$_3$, $R^4$ and $R^5$ represent hydrogen or $R^3$ and $R^4$ together form a radical of the formula —(CH$_2$)$_3$—, $R^5$ represents hydrogen and X represents hydroxyl, and cyclopentane-β-amino acids of the general formula (Ib)

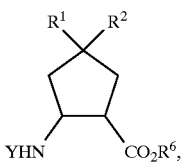
(Ib)

in which $R^1$ and $R^2$ represent hydrogen or $R^1$ and $R^2$ together form a radical of the formula =CH$_2$, $R^6$ represents hydrogen and Y represents hydrogen.

Examples which may be mentioned of such mixtures according to the invention are: a mixture of (S)isoleucine with 2-amino-4-methylenecyclopentane-1-carboxylic acid, (S)-alanine with 2-amino4-methylenecyclopentane-1-carboxylic acid or (S)-proline with 1,2-cis-aminocyclopentane-1-carboxylic acid.

In the case of the mixtures, the molar mixing ratio of α-amino acid and/or derivative thereof to cyclopentane-β-amino acid and/or derivative thereof is in the range from 1:99 to 99:1, preferably 1:10 to 10:1, particularly preferably 1:5 to 5:1 and especially preferably 1:3 to 3:1.

The mixtures according to the invention are usually obtained by mixing the preferably finely powdered individual components.

The present invention also relates to dipeptides comprising an α-amino acid or a derivative thereof and a cyclopentane-β-amino acid or a derivative thereof Suitable α-amino acids for the dipeptides according to the invention are preferably the α-amino acids of the general formula (Ia) mentioned above in the description of the mixtures according to the invention, wherein X in the formula (Ia) represents the content of the covalent bond of the α-amino acid and the cyclopentane-β-amino acid.

Suitable cyclopentane-β-amino acids for the dipeptides according to the invention are preferably the cyclopentane-β-amino acids of the general formula (Ib) mentioned above in the description of the mixtures according to the invention, wherein Y in the formula (Ib) represents the content of the covalent bond of the α-amino acid and the cyclopentane-β-amino acid.

The present invention preferably relates to dipeptides comprising an α-amino acid of the general formula (Ia)

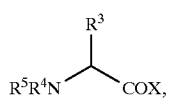
(Ia)

in which $R^3$ represents cycloalkyl having 3 to 8 carbon atoms, or represents aryl having 6 to 10 carbon atoms or hydrogen, or represents straight-chain or branched alkyl having up to 8 carbon atoms, where the alkyl is optionally substituted by cyano, methylthio, hydroxyl, mercapto, guanidyl or by a group of the formula —NR$^7$R$^8$ or R$^9$—OC—, wherein $R^7$ and $R^8$ independently of one another denote hydrogen, straight-chain or branched alkyl having up to 8 carbon atoms or phenyl, and $R^9$ denotes hydroxyl, benzyloxy, alkoxy having up to 6 carbon atoms or the abovementioned group —NR$^7$R$^8$, or the alkyl is optionally substituted by cycloalkyl having 3 to 8 carbon atoms or by aryl having 6 to 10 carbon atoms, which in its turn is substituted by hydroxyl, halogen, nitro, alkoxy having up to 8 carbon atoms or by the group —NR$^7$R$^8$, wherein $R^7$ and $R^8$ have the abovementioned meanings, $R^4$ and $R^5$ represent hydrogen or $R^3$ and $R^4$ together form a radical of the formula —(CH$_2$)$_3$—, $R^5$ represents hydrogen and X represents the content of the covalent bond of the α-amino acid and the cyclopentane-β-amino acid, and cyclopentane-β-amino acids of the general formula (Ib)

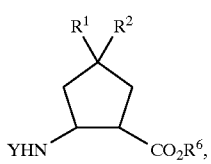
(Ib)

in which $R^1$ and $R^2$ represent hydrogen or $R^1$ and $R^2$ together form a radical of the formula =CH$_2$, $R^6$ represents hydrogen, or represents straight-chain or branched alkyl having up to 8 carbon atoms or phenyl and Y represents the content of the covalent bond of the α-amino acid and the cyclopentane-β-amino acid.

Dipeptides which are more preferred comprise an α-amino acid of the general formula (Ia) in which

7

$R^3$ represents straight-chain or branched alkyl having up to 6 carbon atoms, which is optionally substituted by hydroxyl or phenyl, which in its turn can be substituted by hydroxyl, $R^4$ and $R^5$ represent hydrogen or $R^3$ and $R^4$ together form a radical of the formula —$(CH_2)_3$—, $R^5$ represents hydrogen and X represents the content of the covalent bond of the α-amino acid and the cyclopentane-β-amino acid and a cyclopentane-β-amino acid of the general formula (Ib) in which $R^1$ and $R^2$ represent hydrogen or $R^1$ and $R^2$ together form a radical of the formula =$CH_2$, $R^6$ represents hydrogen, or represents straight-chain or branched alkyl having up to 6 carbon atoms or phenyl and Y represents the content of the covalent bond of the α-amino acid and the cyclopentane-β-amino acid.

Particularly preferred dipeptides comprise an α-amino acid of the general formula (Ia) in which $R^3$ represents methyl, or represents a group of the formula —$CH(CH_3)CH_2CH_3$ $R^4$ and $R^5$ represent hydrogen or $R^3$ and $R^4$ together form a radical of the formula —$(CH_2)_3$—, $R^5$ represents hydrogen and X represents the content of the covalent bond of the α-amino acid and the cyclopentane-β-amino acid, and a cyclopentane-β-amino acid of the general formula (Ib) in which $R^1$ and $R^2$ represent hydrogen or $R^1$ and $R^2$ together form a radical of the formula =$CH_2$, $R^6$ represents hydrogen and Y represents the content of the covalent bond of the α-amino acid and the cyclopentane-β-amino acid.

The following dipeptides are especially preferred:

1,2-cis-2-(S)-isoleucyl-amino-4-methylenecyclopentane-1-carboxylic acid and 1,2-cis-2-(S)-alanyl-amino4methylenecyclopentane-1-carboxylic acid.

The mixtures and dipeptides according to the invention can comprise essentially pure stereoisomers or stereoisomer mixtures.

The α-amino acids, cyclopentane-βamino acids and dipeptides described above can also be in the form of their salts. Salts with organic or inorganic bases or acids and inner salts may be mentioned in general here.

The acids which can be added on include, preferably, hydrogen halide acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, malonic acid, oxalic acid, gluconic acid, succinic acid, fumaric acid, tartaric acid, citric acid, salicylic acid, sorbic acid and lactic acid, and sulphonic acids, such as, for example, p-toluenesulphonic acid, 1,5-naphthalenedisulphonic acid or camphorsulphonic acid.

Physiologically acceptable salts can also be metal or ammonium salts of the compounds according to the invention which have a free carboxyl group. Particularly preferred salts are, for example, sodium, potassium, magnesium or calcium salts, and also ammonium salts, which are derived from ammonia or organic amines, such as, for example, ethylamine, di- or triethylamine, di- or triethanolamine, dicyclohexylamine, dimethylaminoethanol, arginine, lysine, ethylenediamine or phenethylamine.

The mixtures and dipeptides according to the invention can exist in stereoisomeric forms, for example either behave as mirror images (enantiomers) or do not behave as mirror images (diastereoisomers), or can be in the form of a diastereoisomer mixture or pure cis or trans isomers. The invention relates both to the antipodes, racemic forms and diastereomer mixture and to the pure isomers. The racemic forms, like the diastereomers, can be separated into the stereoisomerically uniform constituents in a known manner. Separation into the stereoisomerically uniform compounds is carried out, for example, by means of diastereomeric esters and amides or on optically active phases. Crystallization of diastereomeric salts is also possible.

In the context of the invention, the amino acid radicals defined by the radical ($R^5R^4$—N—$CHR^3$—CO—) are in the L form.

The present invention also relates to a process for the preparation of the dipeptides according to the invention.

These can be prepared by a process in which compounds of the general formula (II)

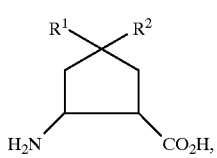

(II)

in which $R^1$ and $R^2$ have the abovementioned meanings, are first converted, by reaction with protected amino acids of the general formula (III)

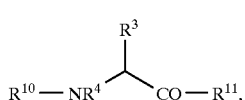

(III)

in which $R^3$ and $R^4$ have the abovementioned meanings, $R^{10}$ represents an amino-protective group and $R^{11}$ represents an activating protective group which is customary in peptide chemistry, preferably the hydroxysuccinimide ester radical, or $R^{10}$ and $R^{11}$ together represent the grouping

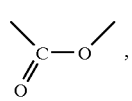

into the compounds of the general formula (IV)

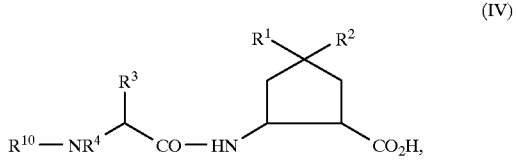

in which

R$^1$, R$^2$, R$^3$, R$^4$ and R$^{10}$ have the abovementioned meanings, in solvents and in the presence of a base, and, finally, the amino-protective group (R$^{10}$) is split off, if appropriate the stereoisomers are separated, and in the case of the esters (R$^6 \neq$H in the formula (Ib)), the acids are reacted with the corresponding alcohols by customary methods.

If appropriate, the dipeptides are converted into the salts by customary methods.

The process according to the invention can be illustrated by way of example by the following equation:

oxycarbonyl, 2,4-dimethoxybenzyloxycarbonyl, 4-methoxybenzyl-oxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, tert-butoxycarbonyl, allyloxycarbonyl, vinyloxycarbonyl, 3,4,5-trimethoxybenzyloxycarbonyl, phthaloyl, 2,2,2-trichloroethoxycarbonyl, 2,2,2-trichloro-tert-butoxycarbonyl, menthyloxycarbonyl, 4-nitrophenoxycarbonyl, fluorenyl-9-methoxycarbonyl (Fmoc), formyl, acetyl, propionyl, pivaloyl, 2-chloroacetyl, 2-bromoacetyl, 2,2,2-trifluoroacetyl, 2,2,2-trichloroacetyl, benzoyl, benzyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl, 4-nitrophenyl or 2-nitrophenylsulphenyl. The Fmoc group is particularly preferred.

Suitable activating carboxyl radicals (R$^{11}$) are in general adducts with carbodiimides, for example N,N'-diethyl-, N,N'-diisopropyl- or N,N'-dicyclohexylcarbodiimide, N-(3-dimethylaminoisopropyl) -N'-ethylcarbodiimide hydrochloride or N-cyclohexyl-N'-(2-morpholinoethyl)carbodiimide metho-p-toluenesulphonate, or carbonyl compounds, such as carbonyldiimidazole, or 1,2-oxazolium cormpounds, such as 2-ethyl-5-phenyl-1,2-oxazolium 3-sulphate or 2-tert-

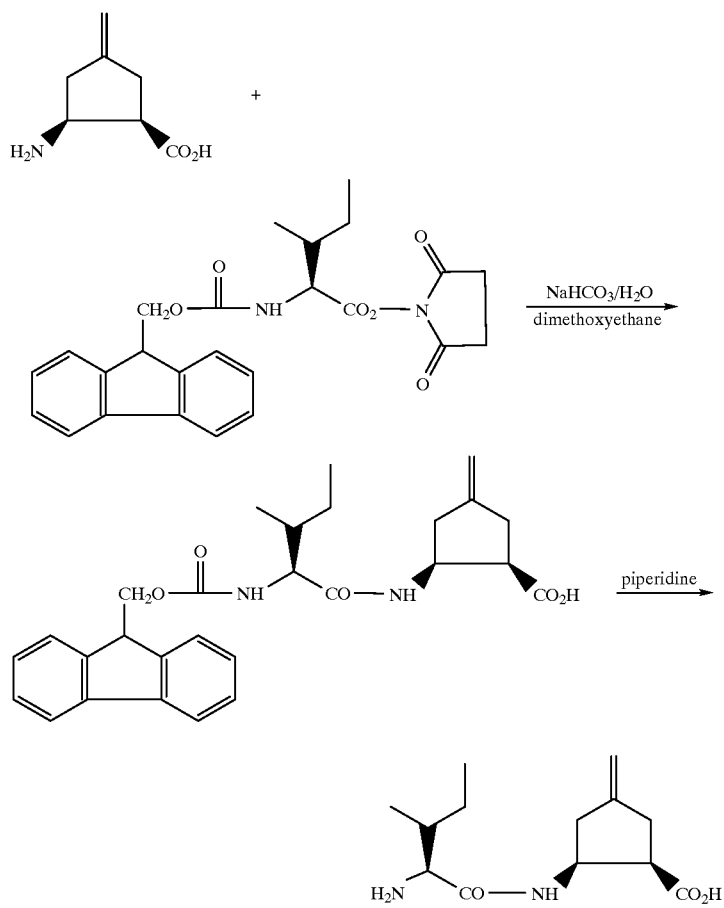

Amino-protective groups (R$^{10}$) in the context of the invention are the customary amino-protective groups used in peptide chemistry.

These include, preferably: benzyloxycarbonyl, 3,4-dimethoxybenzyloxycarbonyl, 3,5-dimethoxybenzylbutyl-5-methylisoxazolium perchlorate, or acylamino compounds, such as 2-ethoxy-1-ethoxycarbonyl-1,2-dihydroquinoline or propanephosphonic anhydride, or isobutyl chloroformate, or benzotriazolyloxy-tris (dimethylamino)phosphonium hexafluorophosphate, 1-hydroxybenzotriazole or hydroxysuccinimide ester. The α-amino acid component can furthermore also be employed in the form of a Leuch anhydride ($R^{10}$ and $R^{11}$ in formula (III) together represent the grouping

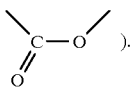

The hydroxysuccinimide ester is preferred.

Suitable solvents are the customary organic solvents which do not change under the reaction conditions. These include, preferably, ethers, such as diethyl ether, dioxane, tetrahydrofuran, glycol dimethyl ether or dimethoxyethane, or hydrocarbons, such as benzene, toluene, xylene, hexane or cyclohexane, or petroleum fractions or dimethylformamide. It is also possible to use mixtures of the solvents mentioned. Tetrahydrofuran, diethyl ether and dimnethoxyethane are preferred. It is furthermore possible to employ water or mixtures of the abovementioned solvents with water.

Furthermore, for example, it is possible to employ alkali metal carbonates, for example sodium or potassium carbonate or bicarbonate, or organic bases, such as trialkylamines, for example triethylamine, ethyldiisopropylamine, N-ethylmorpholine, N-methylpiperidine or N-methylmorpholine. N-methylmorpholine is preferred.

The auxiliaries and bases are employed in an amount of 1.0 mol to 3.0 mol, preferably 1.0 mol to 1.2 mol, per mol of the compounds of the general formula (III).

The reactions are in general carried out in a temperature range from 0° C. to 100° C., preferably at 0° C. to 30° C., under normal pressure.

The reactions can be carried out either under normal pressure or under increased or reduced pressure (for example 0.5 to 5 bar), preferably under normal pressure.

The amino-protective group is in general split off in a manner known per se under acid or basic conditions, or by reduction by catalytic hydrogenation, for example with Pd/C in organic solvents, such as ethers, for example tetrthydrofuran or dioxane, or alcohols, for example methanol, ethanol or isopropanol.

The hydrogenation is in general carried out in a temperature range from 0° C. to 80° C., preferably from 0° C. to 40° C.

The hydrogenation is in general carried out under an increased pressure of 2 bar to 8 bar, preferably 3 to 5 bar.

Bases such as, for example, piperidine, morpholine, dicylohexylamine, p-dimethyl-aminopyridine, diisopropylethylamine or piperazine, are suitable for splitting off the amino-protective group ($R^{10}$=Fmoc). Piperidine is preferred.

The auxiliaries and bases are employed in an amount of 1.0 mol to 3.0 mol, preferably 1.0 mol to 1.2 mol, per mol of the compounds of the general formula (IV).

The reactions are carried out in a temperature range from 0° C. to 100° C., preferably at 0° C. to 30° C., and under normal pressure.

The reactions can be carried out either under normal pressure or under increased or reduced pressure (for example 0.5 to 5 bar), preferably under normal pressure.

The compounds of the general formula (II) are known.

The compounds of the general formula (III) are known in some cases or can be prepared by customary methods.

The above preparation processes are mentioned only for illustration. The preparation of the compounds of the general formulae (Ia) and (Ib) according to the invention in which X and Y together represent a covalent bond is not limited to these processes, and any modification of these processes can be used for the preparation in the same manner.

The starting point of the present invention was the clarification of the following mechanism:

The cyclopentane-β-amino acids of the general formula (II) described are accumulated by various yeast species by amino acid transporters. Transport of the β-amino acids can be inhibited by aliphatic amino acids, in particular L-isoleucine, L-leucine, L-alanine, L-methionine and L-valine. β-amino acids inhibit protein biosynthesis. This inhibition can be antagonized by one of the aliphatic amino acids, in particular by L-isoleucine or L-alanine. Simultaneous administration of β-amino acid and the antagonizing naturally occurring amino acid as a mixture and/or covalently linked as a dipeptide leads to a reduction in the side effects which occur in warm-blooded animals, with the antimycotic action being simultaneously maintained in vivo.

The compounds or m according to the invention therefore display an unforeseeable, valuable pharmacological action spectrum.

The compounds or mixtures of the general formulae (Ia) and (Ib) according to the invention and their acid addition salts have antimicrobial, in particular potent antimycotic, actions in vivo. At the same time, because of their lower toxicity, they have a better tolerability. They have a broad antimycotic action spectrum against dermatophytes, such as *Trichophyton mentagrophytes* and *Microsporum canis*, against yeast fungi, such as *Candida albicans, Candida glabrata* and *Epidermophyton floccosum*, and against moulds, such as *Aspergillus niger* and *Aspergillus fumigatus*. Listing of these microorganisms in no way represents a limitation of the germs which can be combated, but is only of illustrative character. They are therefore suitable for treatment of dermatomycoses and systemic mycoses.

Testing of in-vivo activity

Systemic mouse candidiasis was used as the test model for antimycotic in vivo actions: Male $CFW_1$ mice weighing 20 g were infected by injection of $3 \times 10^5$ CFU of *C. albicans* per animal into the tail vein.

Untreated control animals all died from generalized candidiasis with granuloma formation in the kidneys within one week post infectionem (p.i.). To test the activity, the preparations, dissolved in a 0.2% strength aqueous glucose agar solution, were administered orally by a stomach tube to the infected animals twice daily.

The daily doses were 2×25 mg/kg and 2×50 mg/kg of body weight (BW), and the duration of treatment was 5 days.

The survival rates of the treated animals were recorded daily up to the 10th day p.i. At this point in time, no animals among the untreated control animals survived.

For the preparations, in each case 10 animals were employed per dose and control group.

The results are shown in Table A.

TABLE A

| Example No. | Dose [mg/kg, 2 × daily] | Administration | Number of surviving animals |
|---|---|---|---|
| Control | | | 0/10 |
| 2 | 25 | p.o. | 6/10 |
| 2 | 50 | p.o. | 10/10 |

Alternatively, the in-vivo activity can also be tested on Wistar rats. These would require lower daily doses, based on mg/kg of BW, in order to achieve a comparable effect of treatment. In this case, the test is carried out as follows:

Specifically pathogen-free male Wistar rats eight weeks old and weighing 200 g are infected with 5×10⁶ CFU of Candida albicans in 0.5 ml of PBS via the lateral tail vein. This leads to 100% mortality within eight days. The animals already show haemorrhages in the medial angle of the eye one day after infection; in addition to the kidneys, other organ systems such as the brain, heart, liver, spleen, retina and lung are affected. The substance is administered twice daily for 5 days perorally in 1 ml of glucose (5%)-agar (0.2%) solution in each case, starting on the day of infection.

The better tolerability of the dipeptides or mixtures according to the invention was tested in the following manner:

Wistar rats were fed daily with the corresponding substances and the weight pattern was recorded. Either the β-amino acid by itself or an equimolar amount of the corresponding mixture or dipeptide with an α-amino acid was administered. After a treatment period of 5 days, the body weight of the rats had remained the same or increased slightly in cases where the dipeptides or mixtures according to the invention were administered, while it had decreased by about 5 to 10% in cases of treatment with the β-amino acid.

The present invention also relates to medicaments comprising the mixtures and/or dipeptides according to the invention and to non-toxic, inert pharmaceutical excipients and auxiliaries for combating diseases, in particular mycoses.

If appropriate, the active compound or compounds can also be in microencapsulated form in one or more of the abovementioned excipients.

Preferred pharmaceutical formulations which may be mentioned are tablets, coated tablets, capsules, pills, granules, suppositories, solutions, suspensions and emulsions, pastes, ointments, gels, creams, lotions, powders and sprays.

The therapeutically active compounds or mixtures should preferably be present in the abovementioned pharmaceutical formulations in a concentration of about 0.1 to 99.5, preferably about 0.5 to 95% by weight of the total mixture.

In addition to the compounds according to the invention, the abovementioned pharmaceutical formulations can also comprise other phnrmaceutical active compounds.

The active compounds or the medicaments can be administered orally and parenterally.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, in order to achieve the desired results. An individual dose preferably comprises the active compound or compounds according to the invention in amounts of about 1 to about 80, in particular 3 to 30 mg/kg of body weight.

The medicaments according to the invention are usually combination preparations for simultaneous, separate or staggered use in combating diseases.

Combination preparations for simultaneous use are products in which the individual components of the mixtures according to the invention are present as a physical mixture. These include, in particular, tablets, coated tablets, capsules, pills, suppositories and ampoules. The use of such mixtures as a solution, suspension or emulsion is also conceivable. The individual components of the mixtures according to the invention include, on the one hand, the α-amino acids and/or derivatives thereof, called the α-amino acid component below, and, on the other hand, the cyclopentane-β-amino acids and/or derivatives thereof, called the β-amino acid component below.

Combination preparations for separate use are products in which the individual components of the mixtures according to the invention are present spatially separated from one another. Tablets, coated tablets, capsules, pills and suppositories, which meet this requirement, are particularly suitable for this.

Combination preparations for staggered use are also conceivable. These allow administration of the individual components of the mixtures according to the invention in a sequence spaced with respect to time. In the case of staggered use of such combination preparations, it is conceivable to administer the α-amino acid component in a particular manner in relation to administration of the β-amino acid component. The α-amino acid component can be administered in the same administration form as the β-amino acid component or in another customary administration form, for example the β-amino acid component can be administered intravenously, while the α-amino acid component can be administered perorally or intravenously.

In the case of staggered use, a procedure can also be followed in which only a part dose of the α-amino acid component is administered in the abovementioned relation to administration of the β-amino acid component with respect to time and the remaining amount of the total dose of the α-amino acid component is administered in one or more part doses within a certain period of time after administration of the β-amino acid component.

Starting compounds

EXAMPLE I (−)-1,2-cis-2-((N-(9-Fluorenylmethyloxycarbonyl)-(S)-isoleucyl)-amino-4-ethylenecyclopentane-1-carboxylic acid

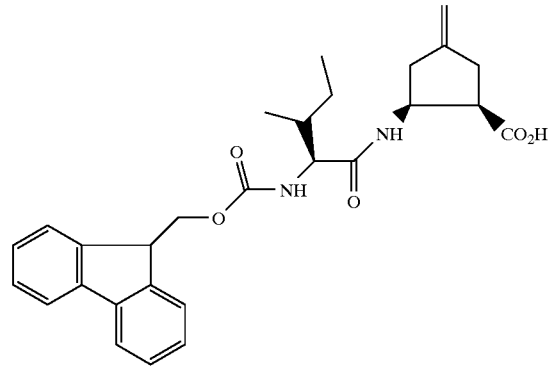

A solution of N-(9-fluorenylmethyloxycarbonyl)(S) isoleucine hydroxysuccinimide ester (89.2 g, 0.198 mol) in 600 ml of dimethoxyethane is added dropwise to a solution of (−)-1,2-cis-2-amino-4methylenecyclopentane-1-carboxylic acid (35.1 g, 0.198 mol) and sodium bicarbonate (33.36 g, 0.397 mol) in 480 ml of water at room temperature. The mixture is stirred overnight at room temperature. The reaction batch is then acidified to pH 2 with dilute hydrochloric acid and extracted several times with diethyl ether. The combined organic phases are dried over sodium sulphate and concentrated in vacuo. The product is crystallized on diethyl ether/petroleum ether.

Yield: 70 g (74% of theory)

Melting point: 207° C.

$[\alpha]_D^{20}$=−24.1 (c=1.15 in chloroform)

$^1$H-NMR (250 MHz, CDCl$_3$): δ=0.88 (cm, 6H); 0.98–1.15, 1.40–1.51, 1.52–1.80 (3m, 3H); 2.40–2.84 (m, 4H); 3.12 (cm, 1H); 4.10–4.48 (m, 4H); 4.61(cm,1H); 4.90 (cm, 2H); 5.84 (d, 1H); 7.20–7.80 (3m, 9H). C$_{28}$H$_{32}$N$_2$O$_5$ (476.6)

EXAMPLE II 1,2-cis-2-(N-(9-Fluorenylmethyl oxycarbonyl)-(S)-alanyl)amino-4-methylene-cyclopentane-1-carboxylic acid

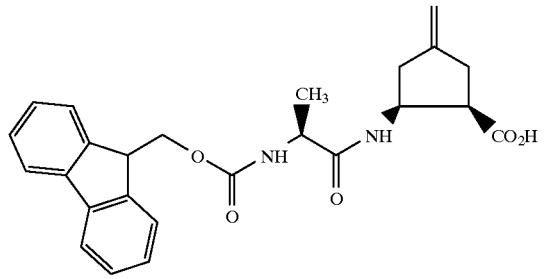

The title compound is prepared analogously to the instructions for Example I from (−)-1,2-cis-2-amino-4-methylenecyclopentane-1-carboxylic acid (2.27 g, 16.1 mmol), N-(9-fluorenylmethyloxycarbonyl)-(S)-alanine hydroxysuccinimide ester (7.0 g, 17.2 mmol) and sodium bicarbonate (1.49 g, 17.7 mmol). The crude product is purified by column chromatography (toluene/ethanol, 9:1).

Yield: 5.7 g (81% of theory)

$^1$H-NMR (500 MHz, CD$_3$OD): δ=1.30 (d, 3H), 2.43–2.79 (m, 4H), 3.10 (cm, 1H), 4.12, 4.21, 4.34, 4.50 (4 cm, 5H), 4.91 (br. s., 2H), 7.30, 7.39, 7.66, 7.79 (4 cm, 8H). C$_{25}$H$_{26}$N$_2$O$_5$ (434.5)

PREPARATION EXAMPLES

Example 1

(+)-1,2-cis-2-(S)-Isoleucyl-amino-4-methylenecyclopentane-1-carboxylic acid

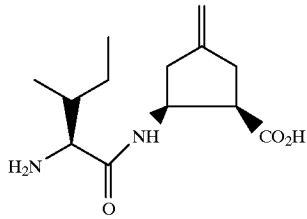

A solution of the compound from Example 1 (24.0 g, 0.050 mol) in piperidine (200 ml) is stirred at room temperature for 1 hour. When the reaction has ended, the piperidine is distilled off in vacuo. The residue is taken up in water. After extraction with diethyl ether several times, the aqueous phase is concentrated in vacuo, with the addition of toluene. The product is crystallized from isopropanol/diethyl ether.

Yield: 8.5 g (67% of theory)

Melting point: 198° C.

$[\alpha]_D^{20}$=+23.9 (c=1.08 in water)

$^1$H-NMR (250 MHz, D$_2$O): δ=0.70–0.88 (m, 6H); 0.91–1.18, 1.19–1.43, 1.53–1.72 (3m, 3H); 2.23–2.67 (m, 4H); 2.88 (cm, 1H); 3.28 (d, 1H); 4.30 (cm, 1H); 4,85 (cm, 2H). C$_{13}$H$_{22}$N$_2$O$_3$ (254.3)

EXAMPLE 2

(+)-1,2-cis-2-(S)-Alanyl-amino-4-methylenecyclopentane-1-carboxylic acid

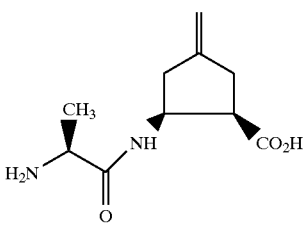

The title compound is prepared analogously to the instructions of Example 1 from Example II (5.7 g, 13.1 mmol). The product is purified by column chromatogrphy over silica gel (methylene chloride/methanol, 1:1) and crystallized from methanol/isopropanol/acetone.

Yield: 0.7 g (25% of theory)

Melting point: 218° C.

$[\alpha]_D^{20}$=+5.4 (c=0.64 in methanol)

$^1$H-NMR (500 MHz, D$_2$O): δ=1.49 (d, 3H), 2.45 (cm, 1H), 2.55–2.75 (m, 3H), 3.04 (cm, 1H), 4.01 (q, 1H), 4.49 (cm, 1H), 5.00 (br, d, 2H) C$_{10}$H$_{16}$N$_2$O$_3$ (212.3)

EXAMPLE 3

(1R,2S)-2-Amino-4-methylenecyclopentane-1-carboxylic acid×(S)-isoleucine

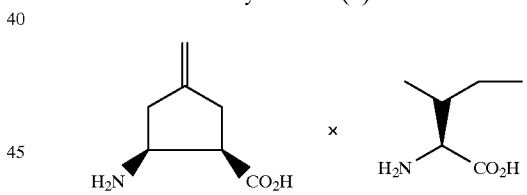

(−)-(1R,2S)-2-amino-4-methylenecyclopentane-1-carboxylic acid (25.0 g, 177 mmol) and (S)-isoleucine (23.2 g, 177 mmol) are dissolved in water (250 ml) and ethanol (100 ml) at the boiling point. The solution is allowed to cool to room temperature and the solvents are distilled off in vacuo at 60° C.

Yield: 48.2 g (100% of theory)

Melting point: 230° C. (decomposition)

$^1$H-NMR (D$_2$O): δ=0.95 (t, 3H), 1.00 (d, 3H), 1.18–1.35, 1.40–1.56 (2 cm, 2H) 1.99 (cm, 1H), 2.52–2.67, 2.73–2.88 (2m, 4H); 3.09 (cm, 1H), 3.69 (d, 1H), 3.88 (cm, 1H), 5.09 (cm, 2H). C$_{13}$H$_{24}$N$_2$O$_4$ (272.3)

EXAMPLE 4

(−)-(1R,2S)-2-Amino-4-methylenecyclopentane-1-carboxylic acid (14.1 g, 100 mmol) and (S)-isoleucine (26.2 g, 200 mmol) are finely powdered and then mixed in pulverulent form.

EXAMPLE 5

A mixture of (−)-(1R,2S)-2-amino-4-methylene-cyclopentane-1carboxylic acid (14.1 g, 100 mmol) and (S)-isoleucine (65.5 g, 500 mmol) is prepared analogously to the instructions of Example 4.

We claim:

1. An antimicrobial mixture comprising α-amino acids and cyclopentane-β-amino acids selected from the group consisting of (S)-isoleucine with 2-amino-4-methylenecyclopentane-1-carboxylic acid, (S)-alanine with 2-amino-4-methylenecyclopentane-1-carboxylic acid and (S)-proline with 1,2-cis-aminocyclopentane-1-carboxylic acid, or a salt thereof and a pharmaceutically acceptable carrier.

2. The mixture according to claim 1 wherein said α-amino acid and cyclopentane-β-amino acid comprises (S)-isoleucine with 2-amino-4-methylenecyclopentane-1-carboxylic acid.

3. A method of treating a microbial infection in a patient suffering therefrom which comprises administering to such patient an antimicrobially effective amount of the mixture according to claim 1.

* * * * *